(12) United States Patent
Gilmore et al.

(10) Patent No.: US 6,420,187 B1
(45) Date of Patent: Jul. 16, 2002

(54) METHOD AND APPARATUS FOR MEASURING VOLATILE COMPOUNDS IN AN AQUEOUS SOLUTION

(75) Inventors: Tyler J. Gilmore, Pasco; Kirk J. Cantrell, West Richland; George R. Holdren, Jr., Kennewick, all of WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/272,761

(22) Filed: Mar. 19, 1999

Related U.S. Application Data

(63) Continuation-in-part of application No. 09/137,717, filed on Aug. 21, 1998, now abandoned.

(51) Int. Cl.⁷ .......................... G01N 1/22; G01N 21/00; B01L 5/02
(52) U.S. Cl. ...................... 436/181; 436/148; 422/68.1; 422/83; 422/99; 422/102; 73/19.1; 73/19.12; 96/257
(58) Field of Search ...................... 422/99, 102, 68.1, 422/83; 73/19.1, 19.12; 96/257; 436/181, 148

(56) References Cited

U.S. PATENT DOCUMENTS

| | | | | |
|---|---|---|---|---|
| 3,653,182 A | * | 4/1972 | Welch ............................ | 53/53 |
| 4,154,086 A | * | 5/1979 | Button et al. ................... | 73/19 |
| 4,253,845 A | * | 3/1981 | Smernoff ...................... | 23/230 |
| 4,266,950 A | * | 5/1981 | Makino et al. ................ | 55/196 |
| 4,330,385 A | * | 5/1982 | Arthur et al. ............... | 204/195 |
| 4,546,640 A | * | 10/1985 | Stone et al. .................... | 73/19 |
| 5,222,032 A | * | 6/1993 | Fleming ..................... | 364/502 |
| 5,258,057 A | * | 11/1993 | Baykut .......................... | 95/89 |
| 5,425,268 A | | 6/1995 | Li et al. ...................... | 73/19.1 |
| 5,646,336 A | * | 7/1997 | Thompson et al. ........ | 73/61.43 |
| 5,777,214 A | * | 7/1998 | Thompson et al. ........ | 73/61.59 |

* cited by examiner

*Primary Examiner*—Jill Warden
*Assistant Examiner*—Monique T. Cole
(74) *Attorney, Agent, or Firm*—Woodard, Emhardt, Naughton, Moriarty & McNett

(57) ABSTRACT

The present invention is an improvement to the method and apparatus for measuring volatile compounds in an aqueous solution. The apparatus is a chamber with sides and two ends, where the first end is closed. The chamber contains a solution volume of the aqueous solution and a gas that is trapped within the first end of the chamber above the solution volume. The gas defines a head space within the chamber above the solution volume. The chamber may also be a cup with the second end. open and facing down and submerged in the aqueous solution so that the gas defines the head space within the cup above the solution volume. The cup can also be entirely submerged in the aqueous solution. The second end of the. chamber may be closed such that the chamber can be used while resting on a flat surface such as a bench. The improvement is a sparger for mixing the gas with the solution volume. The sparger can be a rotating element such as a propeller on a shaft or a cavitating impeller. The sparger can also be a pump and nozzle where the pump is a liquid pump and the nozzle is a liquid spray nozzle open, to the head space for spraying the solution volume into the head space of gas. The pump could also be a gas pump and the nozzle a gas nozzle submerged in the solution volume for spraying the head space gas into the solution volume.

16 Claims, 9 Drawing Sheets

METHOD AND APPARATUS FOR MEASURING VOLATILE COMPOUNDS IN AN AQUEOUS SOLUTION

This application is a continuation-in-part of application Ser. No. 09/137,717, filed Aug. 21, 1998.

This invention was made with Government support under Contract DE-AC0676RL01830 awarded by the U.S. Department of Energy. The Government has certain rights in the invention.

FIELD OF THE INVENTION

The present invention is for analysis of volatile compound content in an aqueous phase wherein the aqueous phase is exposed to a volume of gas and the volatile compound is permitted to enter the gas and to come to an equilibrium concentration within the gas. The gas may then be analyzed to measure gas concentration of volatile compound(s) and the gas concentration related to obtain an aqueous phase concentration. More specifically, the present invention is a method and apparatus for decreasing the amount of time needed to reach equilibrium between the gas and the aqueous phase. As used herein, the term "sparge" includes gas sparge wherein a gas is passed through a liquid and liquid sparge wherein a liquid is passed through a gas.

BACKGROUND OF THE INVENTION

Analysis of a volatile compound in an aqueous solution is well known, generally involving obtaining a sample of the volatile compound laden aqueous solution and placing it in a container with a head space filled with a gas. The volatile compound migrates from the aqueous solution into the gas until an equilibrium concentration is reached between the gas and the aqueous solution. The concentration of volatile compound is then measured in the gas phase and Henry's law is used to obtain the concentration of the volatile compound in the aqueous solution.

Complications arising from solution handling and limited volume of aqueous solution in a sample may be overcome by placing an enclosure or cup in-situ as described in U.S. pat. No. 5,425,268 to Li et al., and shown in FIG. 1. The cup 100 has sides 102 and a top 104 with the bottom 106 open. The cup 100 is submerged into the aqueous solution 108 with the open bottom 106 down so as to trap gas in a head space 110 within the closed top 104 of the cup 100 and trap a solution volume 112 of the aqueous solution near the open bottom end 106 of the cup 100. A vapor sensing transducer 114 is placed in the head space 110 for obtaining measurements of the volatile compound(s). The disadvantage of this approach rermiains the amount of time (days to weeks) for the gas in the head space 110 to reach equilibrium with the solution volume 112.

Accordingly, there is a need in the art of head space analysis of aqueous solutions for a method and apparatus reaching equilibrium in less than several days.

SUMMARY OF THE INVENTION

The present invention is an improvement to the method and apparatus for measuring volatile compounds in an aqueous solution. The apparatus is a chamber with sides and two ends, where the first end is closed. The chamber contains a solution volume of the aqueous solution and a gas that is trapped within the first end of the chamber above the solution volume. The gas defines a head space within the chamber above the solution volume. The chamber may be a cup with the second end open and facing down and submerged in the aqueous solution so that the gas defines the head space within the cup above the solution volume. The cup can also be entirely submerged in the aqueous solution. The second end of the chamber can also be closed such that the chamber can be used while unsubmerged, for example resting on a surface such as a bench. The improvement is a sparger for mixing the gas with the solution lo volume. The sparger can be a rotating element such as a propeller on a shaft or a cavitating impeller. The sparger can also be a pump and nozzle where the pump is a liquid pump and the nozzle is a liquid spray nozzle open to the head space for spraying the solution volume into the head space of gas. The pump could also be a gas pump and the nozzle a gas nozzle submerged in the solution is volume for spraying the head space gas into the solution volume.

An object of the present invention is to provide an apparatus and method for use in head space analysis of aqueous solutions which reduce the time needed to bring the head space gas to an equilibrium concentration of a compound within the aqueous solution.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
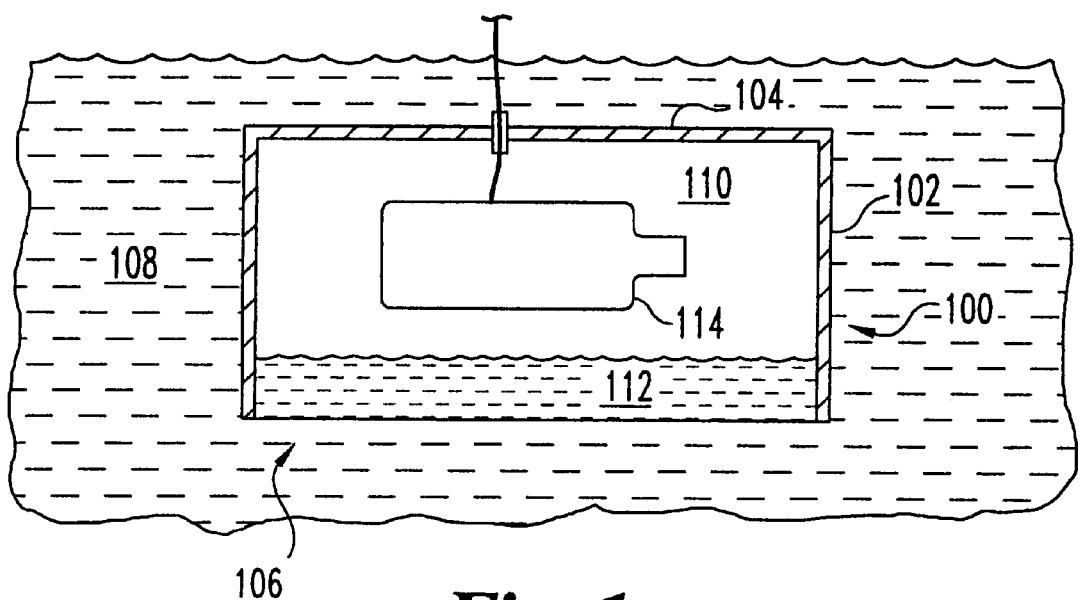
FIG. 1 is a cross section of a prior art cup for volatile compound sampling.
Figure 2A:
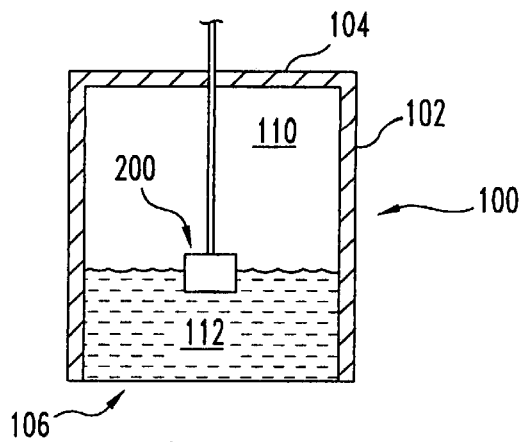
FIG. 2a is a cross section of the volatile compound sampling chamber.

The present invention is an improvement to the method and apparatus for measuring volatile compounds in an aqueous solution. As shown in FIG. 2a, the apparatus is a chamber 100 having sides 102 and a first end 104 that is closed and a second end 106. The chamber contains a solution volume 112 and a gas trapped within the first end 104 above the solution volume 112. The gas defines a head space 110 within the chamber 100 above the solution volume 112. The improvement is a sparger 200 for mixing the gas with solution volume 112. It is important to the present invention that the volume of trapped gas be known and preferred that the volume of trapped gas be constant. Hence it is preferred that none of the trapped gas escape from the head space 110 or from the head space 110 and a closed cycle sampler (not shown) so that the amount of trapped gas remains constant for determination of concentration of volatile compound(s).

Figure 2B:
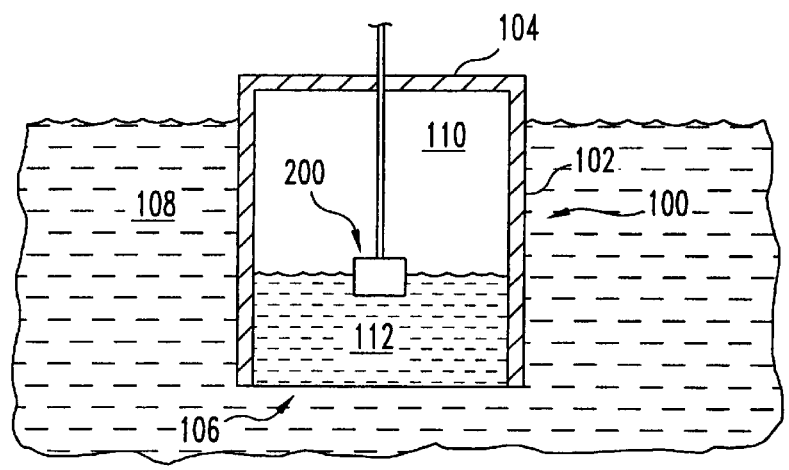
FIG. 2b is a cross section of the volatile compound sampling chamber as a cup with a sparger with the open end of the cup submerged in the aqueous solution.
Figure 2C:
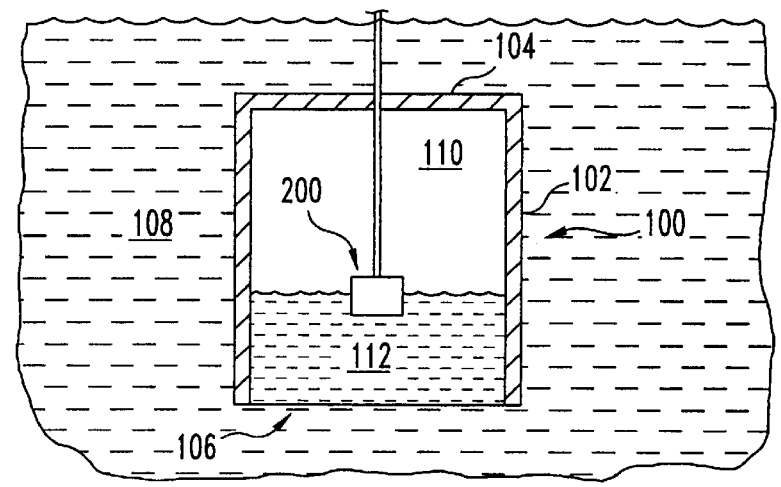
FIG. 2c is a cross section of the volatile compound sampling chamber as a cup with a sparger with the cup entirely submerged in the aqueous solution.
Figure 2D:
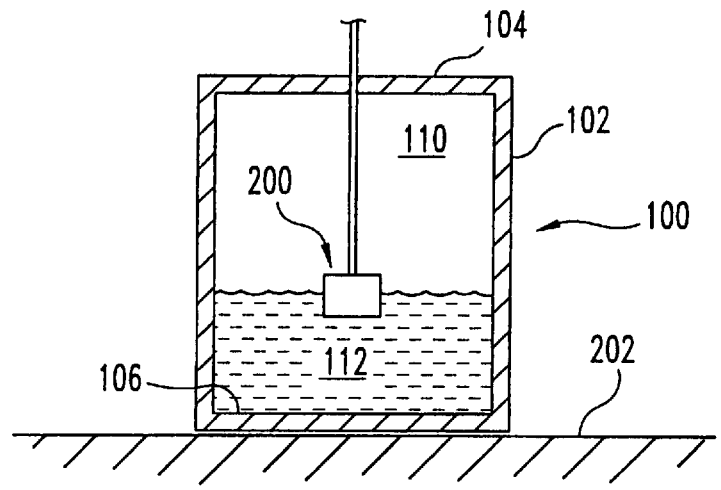
FIG. 2d is a cross section of the volatile compound sampling chamber with a sparger sitting on a bench top.

As shown in FIG. 2b, the chamber 100 may be a cup with the second end 106 open and facing down and submerged in the aqueous solution 108, or the cup may be entirely submerged in the aqueous solution 108 as in FIG. 2c. As shown in FIG. 2d, the second end 106 of the chamber 100 can be closed, permitting measurement of volatile components in the aqueous phase above ground, for example while the chamber 100 is resting on a surface 202 such as a bench top.

Figure 3A:
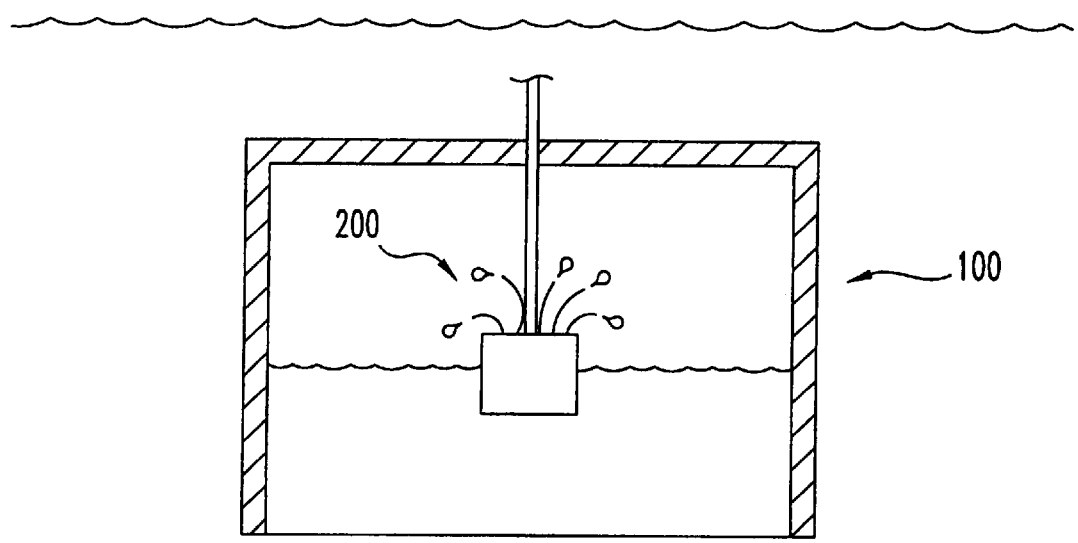
FIG. 3a is a cross section of a chamber as a cup with a spray sparger.
Figure 3B:
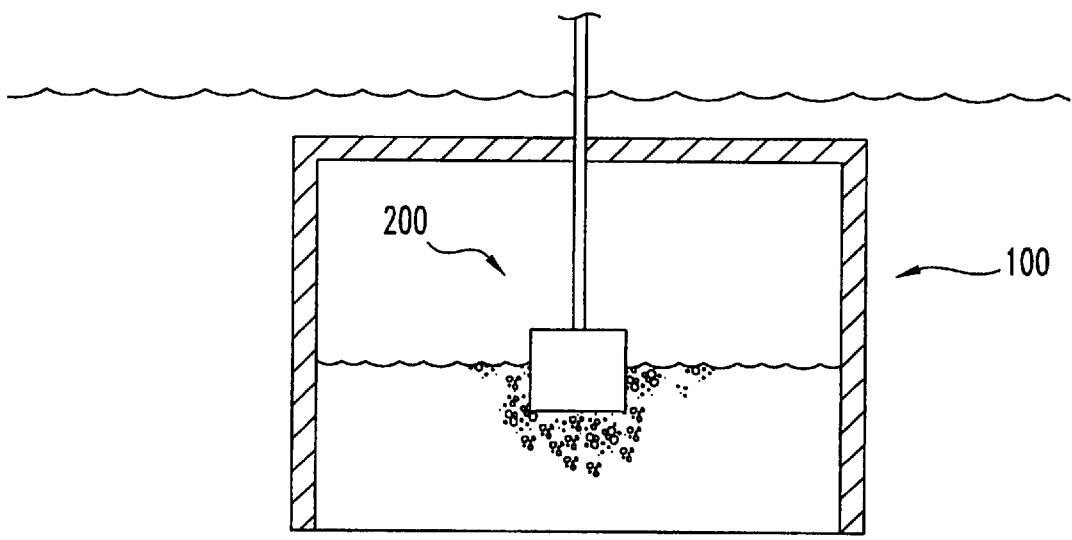
FIG. 3b is a cross section of a chamber as a cup with a bubbling sparger.
Figure 4:
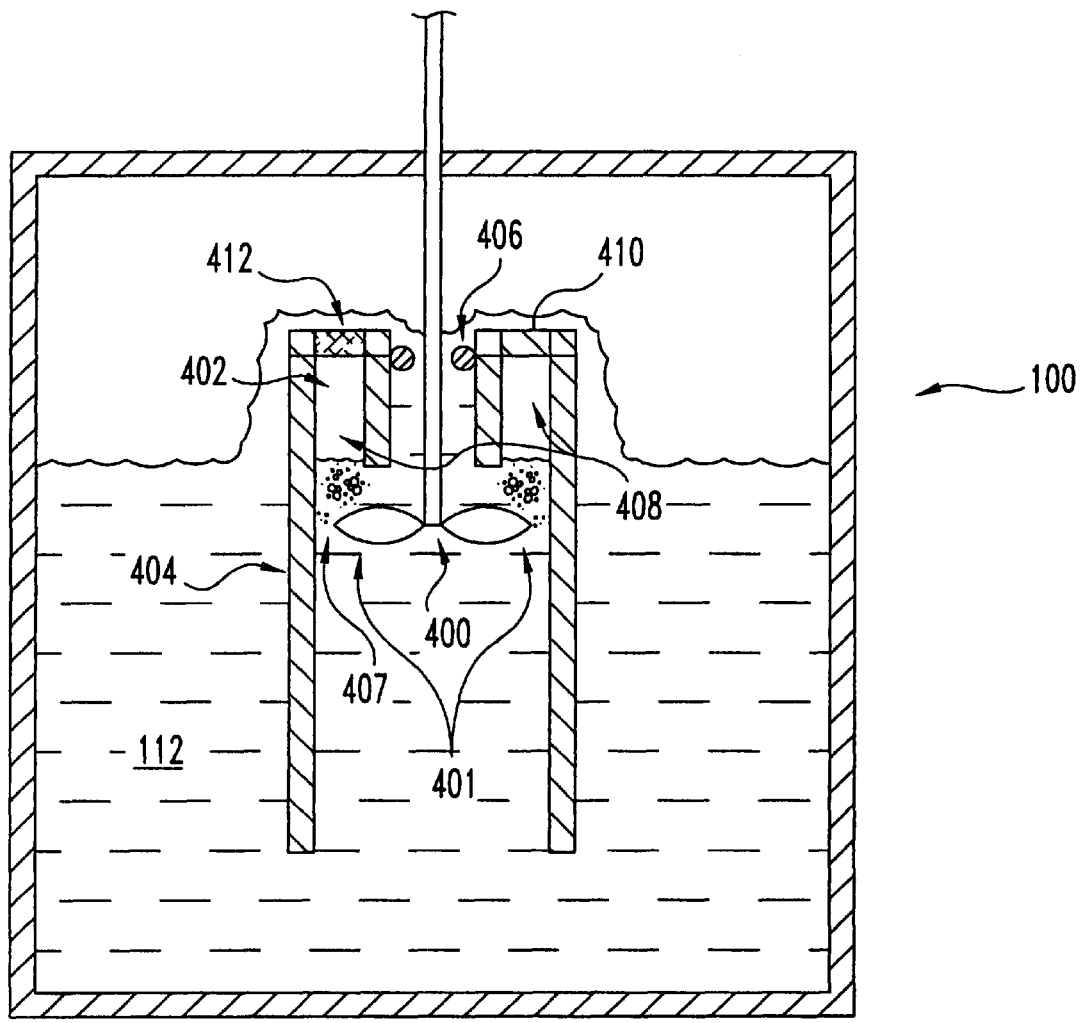
FIG. 4 is a cross section of a chamber with a cavitating impeller sparger.

The sparger 200 may be any device that mixes a liquid with a gas, for example a pump and nozzle, an oscillating element, or a rotating element. The pump may be a liquid pump in combination with a liquid nozzle for spraying the solution volume into the head space (FIG. 3a). The pump may be a gas pump in combination with a gas nozzle submerged in the solution volume which cyclically bubbles the head space gas through the solution volume (FIG. 3b). When pumping the gas, it is preferred to simply recycle or recirculate the head space gas or trapped gas through the solution volume. The oscillating element may be a paddle that is oscillated up and down into and out of the solution volume. The rotating element may be the chamber itself with or without features extending from the sides or top to agitate the gas and solution volume. The rotating element may be a propeller on a shaft or a spinning nozzle. The rotating element may be a cavitating impeller 400 (FIG. 4) with tips 401 designed to create cavitation. Impeller tips designed to create cavitation include tips with sharp edges and high angle surfaces. The apparatus as shown in FIG. 4 includes a cavitating impeller 400 within two concentric tubes 402, 404, an inner tube 402 and an outer tube 404 which is used in a chamber 100. The cavitating impeller 400 extends from the inner tube 402 into the solution volume 112 where it rotates and draws solution up through the inner tube 402 and past a flow meter 406 and out over the top of the inner tube 402 and the outer tube 404 such that the solution is recirculated with the solution volume 112. Gas bubbles 407 are created at the tips of the cavitating impeller 400 and rise through the solution volume 112 to enter a gas chamber 408 formed by the area between the inner tube 402 and the outer tube 404. The gas chamber 408 is capped at its top 410 where a gas sampling port 412 allows for the attachment of sensors or gas collection devices (not shown). The apparatus of FIG. 4 with the cavitating impeller 400 is not limited to use in a chamber 100 where the second end 106 of the chamber 100 is closed,. but may also be used in the chamber 100 configuration as shown in FIG.'s 2b & 2c where the second end 106 of the chamber 100 is open and submerged in the aqueous solution 108. Further, the cavitating impeller 400 itself, without the additional portions of the tube apparatus as depicted in FIG. 4, may be used alone as a sparger 200 in the different chamber 100 configurations of FIG.'s 2a, 2b, 2c & 2d.

Figure 2E:
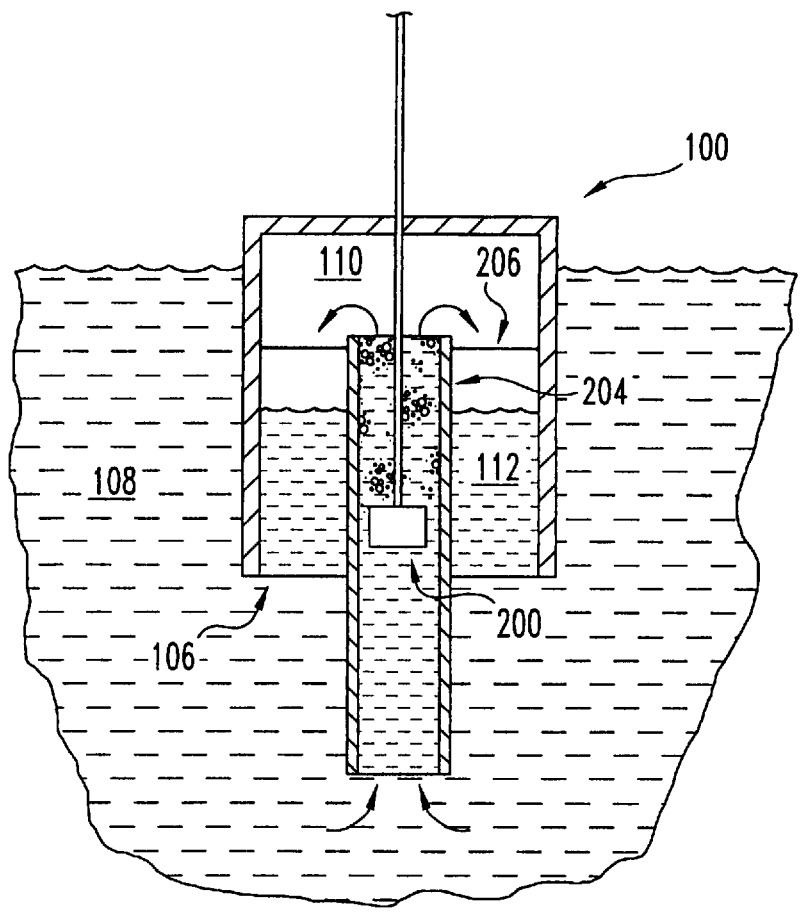
FIG. 2e is a cross section of the volatile compound sampling chamber as a cup with the open end of the cup submerged in the aqueous solution and a to tube around the sparger to create density driven convection of the aqueous solution.

In a preferred embodiment (FIG. 2e), the chamber 100 with the second end 106 open and facing down and submerged in the aqueous solution 108 (FIG. 2b) or the chamber 100 that is entirely submerged in the aqueous solution 108 (FIG. 2c) includes a tube 204 which surrounds the sparger 200 and is attached to the chamber 100 and extends from above the solution volume 112 within the chamber 100 to below the second end 106 of the chamber 100 into the aqueous solution 108. Various means such as spokes 206 can be used for attaching the tube 204 to the chamber 100. In this embodiment, the sparger 200 is preferably a gas pump in combination with a gas nozzle submerged in the solution volume 112 which bubbles the head space gas through the solution volume 112 as in FIG. 3b. Aqueous solution 108 is drawn into the tube 204 by density differences between the solution volume 112 and the aqueous solution 108 created by injecting head space 110 gas through the sparger 200 into the solution volume 112 within the tube 204. The aerated aqueous solution 108 is drawn up the tube 204 by a density driven convection and overflows the top of the tube 204 into the solution volume 112, reducing the time necessary to reach equilibrium of the volatile compound(s) within the head space 110 gas. The top of the tube 204 may additionally have a screen or directional spout (not shown) over it to direct the overflowing aqueous solution 108 down into the solution volume 112. The sparger 200 and the tube 204 are preferably adjustable such that they may be raised or lowered in varying degrees into the solution volume 112 and aqueous solution 108 to control the speed of convection.

In a preferred embodiment (FIG. 5), the sparger 200 is a gas pump 500 most preferably a reciprocal (syringe) type gas pump. in combination with a nozzle 502, submerged in the solution volume 112. The gas pump 500 is connected to the nozzle 502 with a first flow tube 504 through a first check valve 506. A second flow tube 508 open to the head space 110 is connected to the first flow tube 504 through a second check valve 510. First and second check valves 506, 510 control flow direction of the headspace gas which is recirculated through the solution volume. A detector 512 (e.g. gas analyzer) may be placed in the headspace 110, or preferably away from the chamber 100, with a sample tube 514 from the headspace 110 to the detector 512. The nozzle 502 is preferably a porous material, for example a frit.

Figure 6:
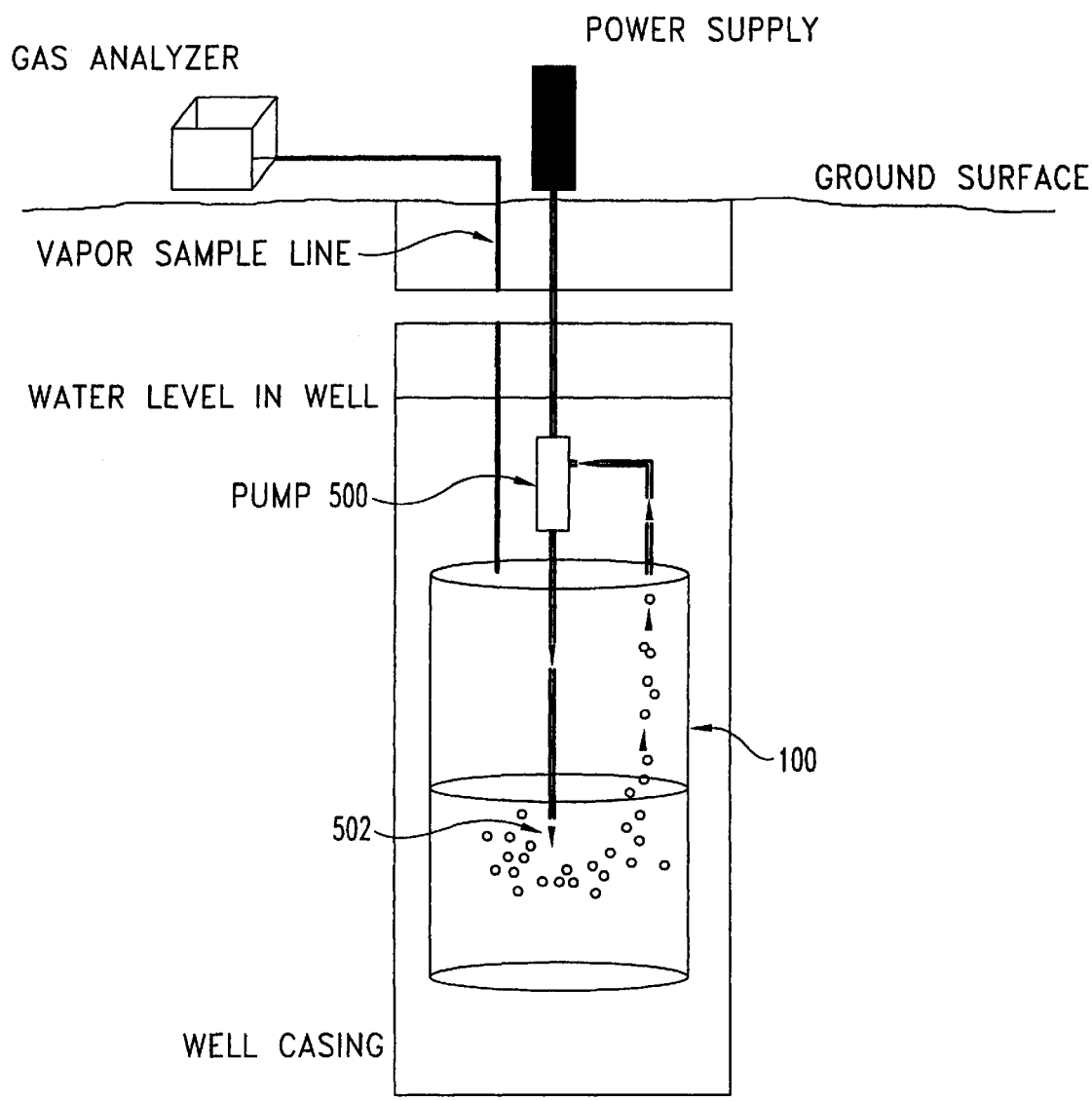
FIG. 6 is a wire frame isometric of an alternative embodiment of a chamber as a cup with a gas pump near the cup.

An alternative embodiment is shown in FIG. 6 wherein the gas pump 500 is on or near the cup 100 controlled or powered remotely. The nozzle 502 may be an open tube end.

Figure 7:
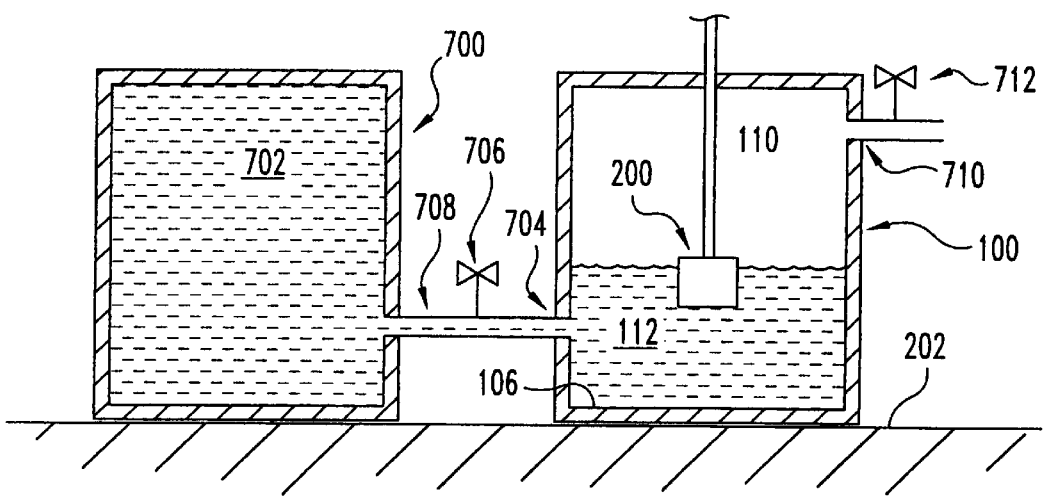
FIG. 7 is a cross section of a preferred embodiment of the volatile compound sampling chamber and sparger sitting on a bench top with a second chamber acting as a clean water reservoir to facilitate gas sampling.

In a preferred embodiment of an above ground chamber 100 with a closed second end 106 as shown in FIG. 2d, a vessel 700 (FIG. 7) is included which contains water 702 used to compensate for pressure changes in the head space 110 of the chamber 100 during sampling. Both the chamber 100 and the vessel 700 may rest on a surface 202 such as a bench top, permitting measurement of volatile components in the aqueous phase above ground versus in a groundwater well for example. In this embodiment, the chamber 100 has an inlet 704 near the closed second end 106. During sampling of the gas in the head space 110, a valve 706 is opened on a connection tube 708 which connects the chamber 100 to the vessel 700, allowing the water 702 from the vessel 700 to enter the chamber 100 and displace the volume of gas in the head space 110 which is being removed for sampling through an outlet 710 in the chamber 100, the outlet 710 which may be controlled by a second valve 712. In this embodiment, the sparger 200 is preferably a pump which cyclically bubbles the lo gas in the head space 110 gas through the solution volume 112.

As will be appreciated by those of skill in the art of chamber type sample units, the chamber 100 may be any geometric shape including but not limited to cylindrical (circular as shown in the Figures or non-circular) oriented vertically (as shown in the FIGS.) or horizontally (quanset hut), conical, parabolic, hyperbolic, spherical pyramidal, and combinations thereof. For horizontal cylinder, conical, parabolic, hyperbolic, spherical, pyramidal and combinations thereof, the distinction between sides and top becomes less clear than for vertically oriented cylinder. For these that have less clear definition, it is herein defined that the sides of these shapes are the portion extending from the open or closed second end or bottom to 45 degrees from the bottom, where the angle is measured by a ray extending radially from the center of the bottom area to the edge of the bottom, and the top of these shapes is the portion extending from 45 degrees from the bottom to the crown, peak or highest extent from the bottom. Thus, recitation of sides and top includes any geometric shape that can form a chamber. It will be further appreciated that the tubes and connections may penetrate the chamber (as shown in the FIGS.) or extend past the sides and enter through the bottom. The chamber material may be any material or. combination of materials, preferably material(s) that does not interfere with the sampling.

The gas may be any gas that is compatible with the sampling procedure. For volatile compounds that are not reactive with oxygen, air is the preferred gas. For volatile compounds that are reactive with oxygen, a non-oxidizing gas may be used, for example nitrogen.

Example 1

Figure 5:
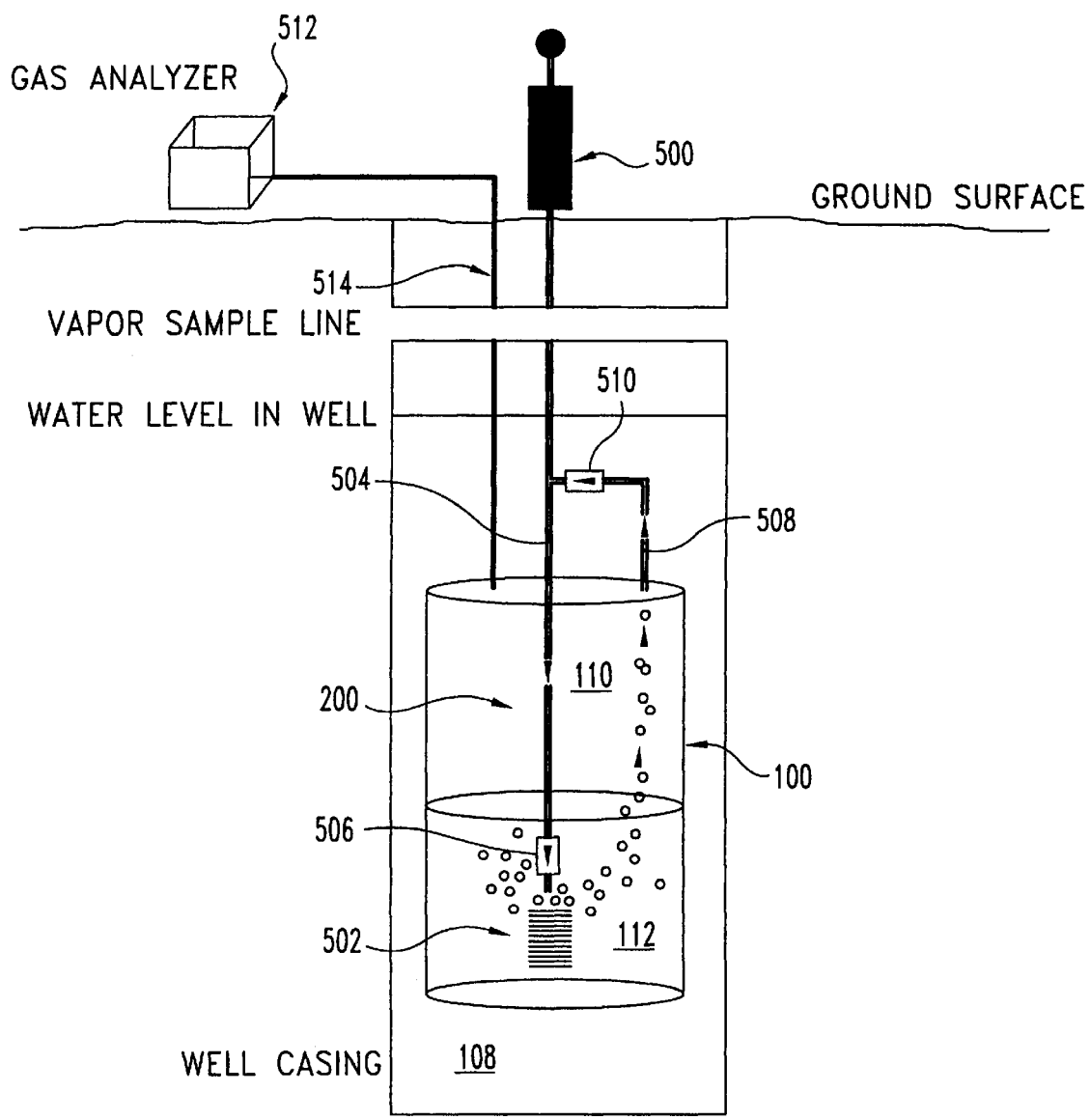
FIG. 5 is a wire frame isometric of a preferred embodiment of a chamber as a cup with a bubbling sparger.

An experiment was conducted to demonstrate the reduced time to equilibrium for volatile compound measurement using the embodiment of FIG. 5. The apparatus was immersed in an aqueous solution of trichloroethylene (TCE) at a concentration of 50 mg/m$^3$, and the gas pump 500 was hand actuated. Air was present in the headspace and used in the gas pump. TCE concentration in the headspace was measured for each stroke of the syringe pump.

Figure 8:
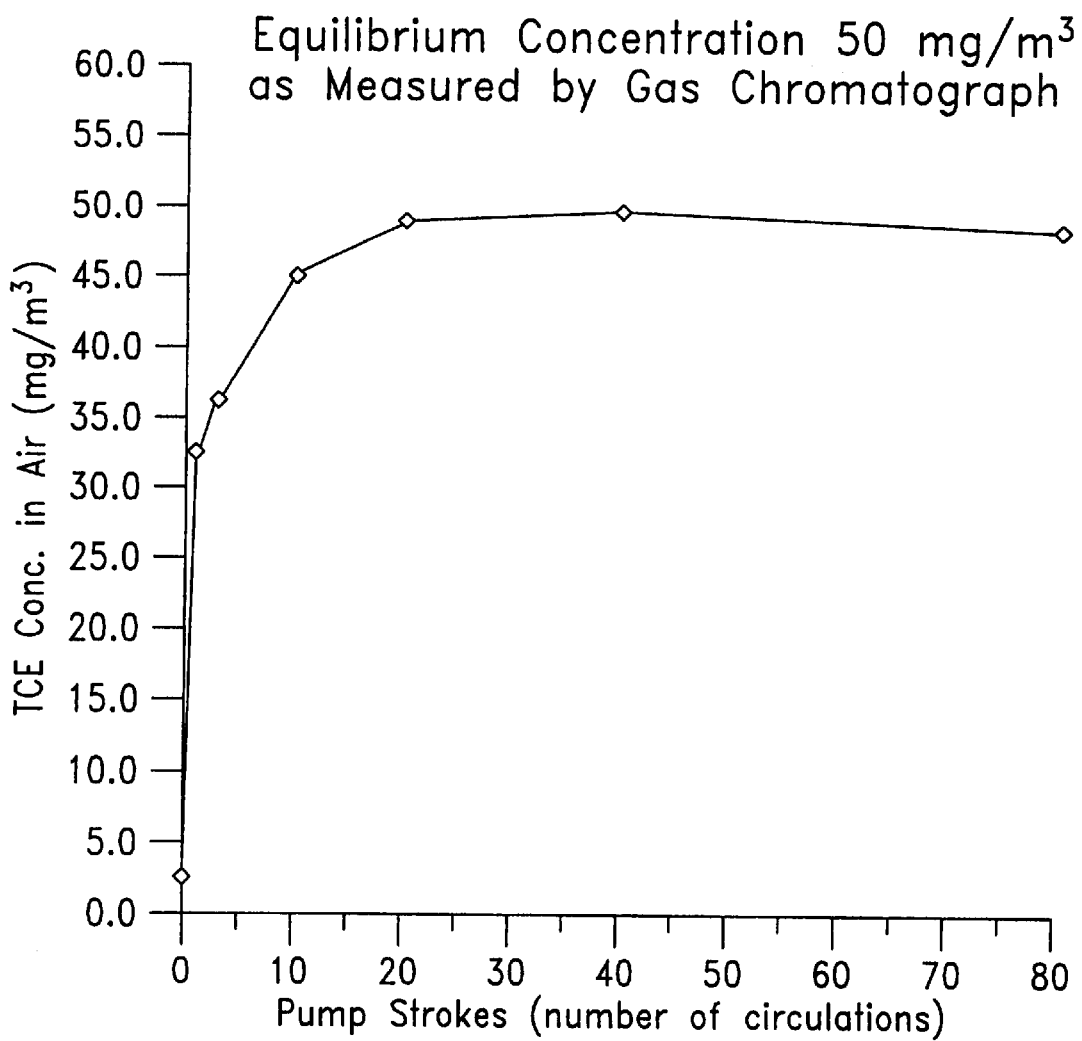
FIG. 8 is a graph of concentration versus pump strokes for a concentration of 50 mgl m³ trichloroethylene.

Results are shown in FIG. 8 showing equilibrium or near equilibrium at about 20 strokes. With. each stroke accomplished in about half a minute, equilibrium was reached in about 10 minutes.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications. as fall within the true spirit and scope of the invention.

We claim:

1. An apparatus for measuring volatile compounds in an aqueous solution, comprising.
   (a) a chamber having sides and a first end that is closed and a second end, said chamber containing a solution volume of said aqueous solution and a gas trapped within said first end above said solution volume, said gas defining a head space within said chamber above said solution volume, wherein said chamber is partially or entirely submerged in said aqueous solution;
   (b) a sparger including a liquid spray nozzle open to said head space; and
   (c) a sensor for measuring a volatile compound in said gas.

2. The apparatus as recited in claim 1, wherein said chamber is a cup with said second end open, said second end facing down and submerged in said aqueous solution.

3. The apparatus as recited in claim 2, wherein said cup is entirely submerged in said aqueous solution.

4. The apparatus us recited in claim 1, wherein said second end of said chamber is closed.

5. A method for measuring volatile compounds in an aqueous solution, comprising:
   (a) containing a solution volume of said aqueous solution and a gas trapped within a chamber, said gas defining a head space above said solution volume within said chamber, wherein said chamber is partially or entirely submerged in said aqueous solution;
   (b) sparging said liquid into said headspace with a liquid spray nozzle open to said head space; and
   (c) measuring a volatile compound in said gas.

6. The method of claim 5 wherein said chamber is a cup with said second end open, said second end facing down and submerged in said aqueous solution.

7. The method of claim 6 wherein said cup is entirely submerged in said aqueous solution.

8. An apparatus for measuring volatile compounds in an aqueous solution, comprising:
   (a) a chamber having sides and a first end that is closed and a second end that is closed, said chamber containing a solution volume of said aqueous solution and a gas trapped within said first end above said solution volume, said gas defining a head space within said chamber above said solution volume;
   (b) a sparger for mixing said gas with said solution volume;
   (c) a vessel containing water connected to said chamber by a connection tube which can be opened and closed by a valve providing fluid communication between said vessel and said chamber; and
   (d) a sensor for measuring a volatile compound in said gas.

9. The apparatus as recited in claim 8, further comprising a tube connected within said cup and surrounding said sparger and extending from said head space above said solution volume to below said second end into said aqueous solution.

10. The apparatus as recited in claim 8, wherein said sparger is a rotating element.

11. The apparatus as recited in claim 10, wherein said rotating element is a propeller on a shaft.

12. The apparatus as recited in claim 10, wherein said rotating element is a cavitating impeller.

13. The apparatus as recited in claim 8, wherein said sparger is a pump and nozzle.

14. The apparatus as recited in claim 13, Wherein said pump is a gas pump and said nozzle is a gas nozzle submerged in said solution volume.

15. The apparatus as recited in claim 14, wherein said gas is recirculated through said solution volume.

16. The apparatus as recited in claim 14, wherein said gas pump is a syringe pump and said nozzle is a porous material submerged in said solution volume, said syringe pump connected to said nozzle with a first flow tube through a first check valve, and a second flow tube open to said head space is connected to said first flow tube through a second check valve.

* * * * *

UNITED STATES PATENT AND TRADEMARK OFFICE
CERTIFICATE OF CORRECTION

PATENT NO. : 6,420,187 B1
DATED : July 16, 2002
INVENTOR(S) : Tyler Gilmore et al.

It is certified that error appears in the above-identified patent and that said Letters Patent is hereby corrected as shown below:

<u>Column 6,</u>
Line 6, replace "us" with -- as --.

Signed and Sealed this

Twenty-eighth Day of January, 2003

JAMES E. ROGAN
*Director of the United States Patent and Trademark Office*